(12) United States Patent
Bartley et al.

(10) Patent No.: US 7,307,183 B2
(45) Date of Patent: Dec. 11, 2007

(54) PROCESS FOR PRODUCING TETRABROMOBENZOATE ESTERS

(75) Inventors: David W. Bartley, West Lafayette, IN (US); James D. Siebecker, West Lafayette, IN (US); Stephen B. Falloon, Lafayette, IN (US)

(73) Assignee: Great Lakes Chemical Corporation, Wilmington, DE (US)

( * ) Notice: Subject to any disclaimer, the term of this patent is extended or adjusted under 35 U.S.C. 154(b) by 470 days.

(21) Appl. No.: 10/629,888

(22) Filed: Jul. 29, 2003

(65) Prior Publication Data

US 2005/0027139 A1   Feb. 3, 2005

(51) Int. Cl.
C07C 69/76   (2006.01)
C07C 67/08   (2006.01)
C08K 5/00    (2006.01)

(52) U.S. Cl. .................. 560/98; 560/83; 560/96; 560/99; 524/288; 524/292

(58) Field of Classification Search .............. 560/83, 560/96, 99, 98; 524/288, 292
See application file for complete search history.

(56) References Cited

U.S. PATENT DOCUMENTS

| | | | | |
|---|---|---|---|---|
| 3,878,261 A | * | 4/1975 | Gardner | 585/749 |
| 4,375,551 A | * | 3/1983 | Finley | 560/83 |
| 5,049,697 A | | 9/1991 | Bohen et al. | |
| 5,208,366 A | | 5/1993 | Bohen et al. | |
| 5,329,054 A | | 7/1994 | Theriot et al. | |
| 5,637,757 A | | 6/1997 | Hill et al. | |
| 5,728,323 A | * | 3/1998 | Day et al. | 252/601 |
| 5,728,760 A | * | 3/1998 | Rose et al. | 524/292 |

FOREIGN PATENT DOCUMENTS

| | | |
|---|---|---|
| JP | 64-025737 | 1/1989 |
| WO | WO96/32438 | 10/1996 |
| WO | WO 98/57920 A2 | 6/1998 |

OTHER PUBLICATIONS

March et al ,March's Advanced Orgainc Chemistry, 1992 A Wiley-International Science Pub. 4th ed. ,p. 219.*
Wikipedia, the free encyclopedia, Sodium Carbonate, Nov. 2006, p. 1-2.*
Spatz et al ,Use of Tetrabromophthalic Anhydride (TBPA) in the Construction of Fire-Retardant Polyester and Epoxy Resins, 1969,Ind. Eng. Chem. Prod. Res. Dev. , vol. 8, No. 4, p. 381-391.*

* cited by examiner

Primary Examiner—Taylor Victor Oh
(74) Attorney, Agent, or Firm—Baker & Daniels LLP

(57) ABSTRACT

A method for preparing tetrabromobenzoate ester from a tetrabromophthalic anhydride including the steps of reacting the tetrabromophthalic anhydride with a catalyst and an alcohol at a temperature that favors partial esterification over complete esterification of the tetrabromophthalic anhydride to form a tetrabromophthalate half-ester reaction mixture; and feeding the half-ester reaction mixture to at least one reactor having and maintaining a temperature that favors decarboxylation over esterification to produce a tetrabromobenzoate ester-containing product. The temperature favoring partial esterification of the tetrabromophthalic anhydride is between about 70° C. and 130° C. The temperature favoring decarboxylation over esterification is between about 190° C. and 205° C. The tetrabromobenzoate ester-containing product comprises at least about 85% tetrabromobenzoate ester. The at least one reactor may include two or more reactors connected to one another in series.

17 Claims, No Drawings

PROCESS FOR PRODUCING TETRABROMOBENZOATE ESTERS

BACKGROUND OF THE INVENTION

1. Field of the Invention

The present invention relates to methods for synthesizing tetrabromobenzoate esters and, more particularly, to a method for synthesizing tetrabromobenzoate esters from tetrabromophthalic anhydride using a process that provides high yields.

2. Description of the Related Art

Tetrabromobenzoate esters have been formed as minor by-products in the synthesis of tetrabromophthalate diesters from tetrabromophthalic anhydride. However, these by-products are considered undesirable in the synthesis of tetrabromophthalate diesters and, therefore, the process has been refined to avoid the production of tetrabromobenzoate esters.

Tetrabromobenzoate esters have also been synthesized directly through the esterification of tetrabromobenzoic acid using a metal or organometallic esterification catalyst. Unfortunately, tetrabromobenzoic acid is not readily available and, therefore, must be synthesized prior to esterification. In addition, the esterification of tetrabromobenzoic acid requires long reaction times and the metal or organometallic esterification catalyst is relatively expensive and often requires complicated, time-consuming removal and disposal procedures.

Alternatively, tetrabromobenzoate ester compounds have been prepared from tetrabromophthalic anhydride using a one-pot batch synthesis in which tetrabromophthalic anhydride is reacted in a single reactor with an appropriate alcohol in the presence of a decarboxylation catalyst to form the tetrabromobenzoate ester. More specifically, the tetrabromophthalic anhydride is reacted with the alcohol at low reactor temperatures to form a half-ester intermediate. The reactor is then heated to higher temperatures and the half-ester intermediate, in the presence of a decarboxylation catalyst, forms the tetrabromobenzoate ester. However, this reaction scheme yields a product containing the target compound tetrabromobenzoate ester and a significant amount of tetrabromophthalate diester. In addition, the reaction product often has an undesirable amber color.

Therefore, a need remains for a more efficient process for producing tetrabromobenzoate esters. More specifically, a need remains for a method for synthesizing tetrabromobenzoate esters at higher yield ratios of tetrabromobenzoate ester to tetrabromophthalate diester, and/or a more desirable lighter color.

SUMMARY OF THE INVENTION

The present provides a method for preparing tetrabromobenzoate ester from tetrabromophthalic anhydride comprising the steps of combining the tetrabromophthalic anhydride and an alcohol in at least one reaction vessel to form a first reaction mixture; heating the first reaction mixture to a temperature that favors partial esterification over complete esterification to form a tetrabromophthalate half-ester intermediate mixture; feeding the tetrabromophthalate half-ester intermediate mixture and a catalyst to at least one heated reactor having a temperature that favors decarboxylation over esterification; and maintaining the at least one reactor at the temperature that favors decarboxylation over esterification to produce a tetrabromobenzoate ester-containing product.

The temperature that favors partial esterification over complete esterification is between about 70° C. and about 130° C., and the temperature that favors decarboxylation over esterification is between about 190° C. and about 205° C. The method of the present invention may be conducted continuously, semi-continuously or in batch. The alcohol has the general formula ROH, wherein R is an organic group having up to about 30 carbon atoms. The catalyst may be any compound that promotes the decarboxylation reaction over the esterification reaction. Appropriate catalysts may include carbonates, alkali bicarbonates, alkalis, and mixtures thereof.

The present invention further provides a method for the preparation of tetrabromobenzoate esters comprising the steps of feeding either tetrabromophthalic anhydride, tetrabromophthalic diacid, or mixture thereof, and an alcohol to at least one reactor wherein the first of the at least one reactor contains a product mixture, the product mixture comprising tetrabromobenzoate ester, the at least one reactor having a temperature that favors decarboxylation over esterification; and maintaining the at least one reactor at the temperature that favors decarboxylation over esterification to produce a tetrabromobenzoate-containing product.

DETAILED DESCRIPTION

The embodiments hereinafter disclosed are not intended to be exhaustive or limit the invention to the precise forms disclosed in the following description. Rather the embodiments are chosen and described so that others skilled in the art may utilize its teachings.

The present invention is directed to a method for converting tetrabromophthalic anhydride to a selected tetrabromobenzoate ester. In general, the conversion of tetrabromophthalic anhydride to tetrabromobenzoate ester includes two steps. The first step involves the partial esterification of tetrabromophthalic anhydride with an appropriate alcohol to produce the intermediate, tetrabromophthalate half-ester, which also bears a carboxylic acid group. In the second step, depending on the reaction conditions the half-ester intermediate proceeds, in the presence of a decarboxylation catalyst, by either a decarboxylation or esterification reaction to produce the selected tetrabromobenzoate ester or tetrabromophthalate diester, respectively. As is described in further detail below, the process of the present invention favors the decarboxylation reaction and, therefore, produces a higher product ratio of tetrabromobenzoate to tetrabromophthalate diester. The general synthetic process is shown in Scheme I below, wherein the group R generally represents an organic group having up to about 30 carbon atoms:

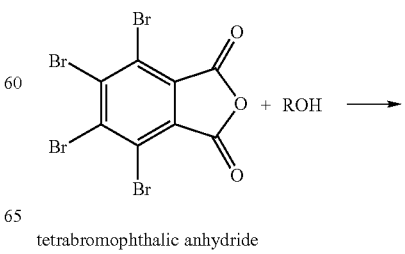

tetrabromophthalic anhydride

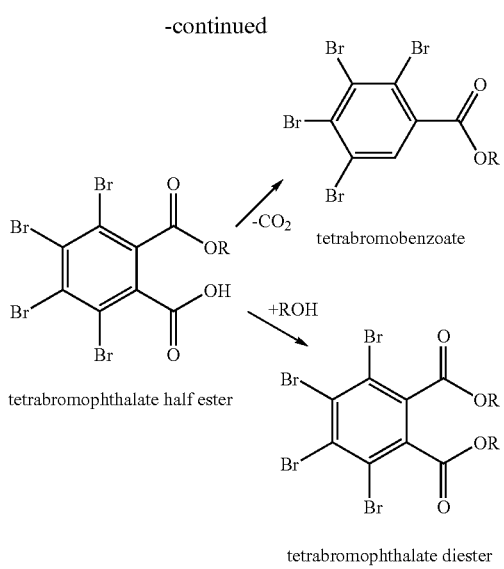

In one embodiment, the first step of the process involves combining the tetrabromophthalic anhydride and an alcohol in a suitable reaction vessel to form a first reaction mixture, and subjecting the first reaction mixture to conditions that favor the formation of the tetrabromophthalate half-ester. In other words, the tetrabromophthalic anhydride is reacted with an alcohol under conditions that favor the partial, rather than complete, esterification of the tetrabromophthalic anhydride. Such conditions may include a reaction temperature below about 130° C. Particularly, it has been found that heating the first reaction mixture to a temperature between about 70° C. and about 130° C. favors partial esterification rather than complete esterification. In addition, heating the reaction mixture to between about 90° C. and about 130° C. has produced particularly favorable results. Reaction temperatures between about 90° C. and about 120° C. may produce even more favorable results. Furthermore, factors such as the reactivity of the particular alcohol used and the amount of excess alcohol present in the reaction may influence the optimum temperature. The reaction temperature may be maintained for about 1-4 hours or until formation of the half-ester is complete. The resulting tetrabromophthalate half-ester intermediate mixture preferably comprises a conversion of at least about 50 mole % of the tetrabromophthalic anhydride to the half-ester, and more preferably about a 95 mole % conversion.

Once the half-ester is formed, it may be useful to maintain the half-ester intermediate mixture at an elevated storage temperature to prevent the formation of solids. The ideal storage temperature will depend upon factors such as the alcohol used in the reaction and the amount of excess alcohol present in the half-ester intermediate mixture. For instance, it has been found that when 2-ethylhexanol is used, maintaining the storage temperature above 90° C. helps to prevent crystallization of the half-esters, while maintaining the storage temperature below 120° C. helps to prevent or limit formation of the phthalate diester.

Suitable reaction vessels for the partial esterification step include stirred tank reactors and hot tube reactors. This partial esterification step may be conducted in batch, semi-continuous, or continuous fashion. When run continuously, one or more stirred tank reactors connected in series may be employed, or alternatively, a series of tube reactors may be used.

In general, no catalyst is needed to promote the formation of the half-ester. However, because current commercial tetrabromophthalic anhydride typically contains a small amount of residual mineral acid from the manufacturing process, it may be useful to add a small amount of weak base to neutralize the acid. If left unneutralized, the acid may promote formation of the corresponding ether from two molecules of the selected alcohol, the ether having the formula R—O—R, with the R group being described below. The weak base used to neutralize the acid may also function as the catalyst for promoting decarboxylation over esterification in the second step. As discussed in further detail below, alkali carbonates, alkali bicarbonates and caustic alkalis can serve as the neutralizing agent/decarboxylation catalyst. Sodium and potassium carbonate and bicarbonate, lithium carbonate and sodium aluminate may be particularly useful. The amount of weak base to be added depends upon the amount of residual mineral acid contained in the particular lot of tetrabromophthalic anhydride being used. The manufacturer of the tetrabromophthalic anhydride typically provides this information. Based on the acid content, the amount of weak base may then be calculated to provide from about 1.0 to about 1.5 equivalents of base per equivalent of acid. Larger amounts may be used, but may result in the need for additional purification of the reaction product.

The alcohol used in the partial esterification step has the general formula ROH, in which R is an organic group having up to about 30 carbon atoms in a linear or branched arrangement. The organic group of the alcohol may also be substituted with one or more groups such as alkoxy, halo, amino, thio, and the like. Alcohols particularly useful in the present invention include alcohols having a boiling point of above about 160° C. Of these alcohols, those having a boiling point below about 230° C. are preferred. These alcohols allow the decarboxylation reaction to proceed at a reasonable rate, while still allowing for ease of stripping the excess alcohol from the product at the end of the reaction. Particularly useful alcohols are non-halogenated, non-sulfur-containing, and non-nitrogen-containing alcohols. Branched chain alcohols are particularly useful. Mixtures of alcohols having less than perfect separation may also be used.

Appropriate alcohols with boiling points between about 160° C. and about 230° C. include 2-(2-methoxy)ethoxyethanol, 2-butoxyethanol, 3,3-diethoxy-1-propanol, di(propylene glycol) methyl ether, 2-ethyl-1-hexanol, 3-ethyl-1-hexanol, 3,4-dimethyl-1-hexanol, 3,5-dimethyl-1-hexanol, 3-methyl-1-heptanol, 4-methyl-1-heptanol, 2-octanol, 5-methyl-1-heptanol, 3-octanol, 2-propyl-1-pentanol, 2,6-dimethyl-4-heptanol, 2-nonanol, dihydromyrcenol, 3,5,5-trimethyl-1-hexanol, 3,7-dimethyl-1-octanol, 3,7-dimethyl-3-octanol, mixed $C_7$ and $C_9$ alcohols (hereinafter "mixed $C_7/C_9$ alcohols"), isooctyl alcohol, mixed $C_9$ alcohols, 3-furanmethanol, furfuryl alcohol, tetrahydrofurfuryl alcohol, 3-acetyl-1-propanol, 2-isopropoxyethanol, 3-methoxy-1-butanol, 2-cyclohexen-1-ol, 1,5-hexadien-3-ol, t,t-2,4-hexadien-1-ol, 3-hexyn-1-ol, 5-hexyn-1-ol, cyclopentanemethanol, 4-methyl-1-pentanol, 3-(trimethylsilyl)allyl alcohol, benzyl alcohol, 3-trimethylsilyl-1-propanol, 3-cyclohexen-1-methanol, 3-methyl-2-cyclohexen-1-ol, cycloheptanol, cyclohexylmethanol, 1-methylcyclohexanol, 2-methylcyclohexanol, 3-methylcyclohexanol, 4-methylcyclohexanol, 1-heptanol, 2-heptanol, propylene glycol butyl ether, 2-methylbenzyl alcohol, 3-methylbenzyl alcohol, 4-methylbenzyl alcohol, phenethyl alcohol, sec-phenethyl alcohol, 1-octyn-3-ol, cycloheptanemethanol, 2-cyclohexylethanol, 1-cyclohexylethanol, cyclooctanol, 3-cyclopentyl-1-propanol, 2,3-dimethylcyclohexanol, 2,6dimethylcyclohexanol, 3,5-dimethylcyclohexanol, 2ethylcyclohexanol, 4-ethylcyclohexanol, 1-octanol, 6-methyl-5-hepten-2-ol, 1-octen-3-ol, 6-methyl-2-heptanol, 2-(cyclohexyloxy)ethanol, 2,2-dimethoxycyclohexanol, 2,4,4-trimethyl-1-pentanol, 1-phenyl-1-propanol, 1-phenyl-2-propanol, 2-phenyl-2-propanol, 3-nonyn-1-ol, 2,4-dimethyl-2,6-heptadien-1-ol, 3-cyclohexyl-1-propanol, 3,5,5-trimethyl-2-cyclohexen-1-ol, 3-nonen-1-ol, 3-ethyl-2,2-dimethyl-3-pentanol, 1-nonanol, 1-myrtenol, 2-phenyl-3-butyn-2-ol, 1-phenyl-1-cyclopropanemethanol, 2-methyl-1-phenyl-2-propanol, isopulegol, linalool, 1-myrtenol, nerol, terpineol, terpinen-4-ol, citronellol, 4-cyclohexyl-1-butanol, 2-decanol, 4-decanol, mixed $C_7$-$C_{11}$ alcohols, isodecyl alcohol, hexyl decyl alcohol, 1,3-dibromo-2-propanol, 2,3-dibromopropanol, 1,3-dichloro-2-propanol, 1,3-difluoro-2-propanol, 3-bromo-1-propanol, 3-chloro-1-propanol, 4-chloro-1-butanol, 2-(methylthio)ethanol, 3-bromo-3-buten-1-ol, 3-pyrrolidinol, 1,4-dibromo-2-butanol, 2-(2-chloroethoxy)ethanol, 3-methylthio-1-propanol, 3-thiophenemethanol, 2,2-bis(chloromethyl)-1-propanol, tetrahydro-4H-pyran-4-ol, 3-bromo-2,2-dimethyl-1-propanol, 2-(3-thienyl)ethanol, 3-chloro-2,2-dimethyl-1-propanol, 1-methyl-3-pyrrolidinol, 4-(methylthio)-1-butanol, 2-(trimethylsilyl)ethanol, 2-(2-thienyl ethonol, tetrahydropyran-2-methanol, 6-bromo-lhexanol, 6-chloro-1-hexanol, 7-bromo-1-heptanol, N,N-diethylethanolamine, 1-methyl-2-pyrrolidinemethanol, 1-piperideneethanol, 3-(methylthio)-1-hexanol, 3-diethylamino-1-propanol, 2-(diisopropylamino)ethanol and 2-{[2-(dimethylamino)ethyl]methylamino}ethanol. Of these, 3-furanmethanol, furfuryl alcohol, tetrahydrofurfuryl alcohol, 3-acetyl-1-propanol, 2-isopropoxyethanol, 3-methoxy-1-butanol, 2-cyclohexen-1-ol, 1,5-hexadien-3-ol, t,t-2,4-hexadien-1-ol, 3-hexyn-1-ol, 5-hexyn-1-ol, cyclopentanemethanol, 4-methyl-1-pentanol, 3-(trimethylsilyl)allyl alcohol, cyclohexylmethanol, 3-trimethylsilyl-1-propanol, benzyl alcohol, 3-cyclohexen-1-methanol, 3-methyl-2-cyclohexen-1-ol, cycloheptanol, 1-methylcyclohexanol, 2-methylcyclohexanol, 3-methylcyclohexanol, 4-methylcyclohexanol, 1-heptanol, 2-heptanol, propylene glycol butyl ether, 2-methylbenzyl alcohol, 3-methylbenzyl alcohol, 4-methylbenzyl alcohol, phenethyl alcohol, sec-phenethyl alcohol, 1-octyn-3-ol, cycloheptanemethanol, 2-cyclohexylethanol, 1-cyclohexylethanol, cyclooctanol, 3-cyclopentyl-1-propanol, 2,3-dimethylcyclohexanol, 2,6-dimethylcyclohexanol, 3,5-dimethylcyclohexanol, 2-ethylcyclohexanol, 4-ethylcyclohexanol, 6-methyl-5-hepten-2-ol, 1-octen-3-ol, 2-(cyclohexyloxy)ethanol, 2,2-dimethoxycyclohexanol, 6-methyl-2-heptanol, 1-octanol, 2,4,4-trimethyl-1-pentanol, 1-phenyl-1-propanol, 1-phenyl-2-propanol, 2-phenyl-2-propanol, 2,4-dimethyl-2,6-heptadien-1-ol, 3-nonyn-1-ol, 3,5,5-trimethyl-2-cyclohexen-1-ol, 3-cyclohexyl-1-propanol, 3-nonen-1-ol, 1-nonanol, 3-ethyl-2,2-dimethyl-3-pentanol, 2-phenyl-3-butyn-2-ol, 1-phenyl-1-cyclopropanemethanol, 1-myrtenol, isopulegol, 2-methyl-1-phenyl-2-propanol, linalool, 1-myrtenol, nerol, terpineol, terpinen-4-ol, citronellol, 2-decanol, 4-decanol, 4-cyclohexyl-1-butanol, mixed $C_7$/$C_{11}$ alcohols, isodecyl alcohol and hexyl decyl alcohol are preferred, while 3,3-diethoxy-1-propanol, 2-(2-methoxy)ethoxyethanol, 3,4-dimethyl-1-hexanol, 2-butoxyethanol, di(propylene glycol) methyl ether, 3-ethyl-1-hexanol, 2-ethyl-1-hexanol, 3,5-dimethyl-1-hexanol, 3-methyl-1-heptanol, 4-methyl-1-heptanol, 5-methyl-1-heptanol, 2-octanol, 3-octanol, 2-propyl-1-pentanol, 2,6-dimethyl-4-heptanol, 2-nonanol, 3,5,5-trimethyl-1-hexanol, dihydromyrcenol, 3,7-dimethyl-1-octanol, 3,7-dimethyl-3-octanol, mixed $C_7$/$C_9$ alcohols, isooctyl alcohol and mixed $C_9$ alcohols are most preferred.

Some increase in selectivity towards the benzoate has been observed when certain alcohols are used. For example, 2-butoxyethanol or 2-methoxyethoxyethanol show high selectivity towards the benzoate, and are, therefore, particularly useful.

According to another embodiment of the present invention, the first step of the process may be carried out in an inert solvent, such as a high boiling ether, in near stoichiometric amounts of the alcohol (e.g., 1.0 to 1.25 mole equivalents). Inert solvents particularly useful in the present invention have a boiling point of between about 160° C. and about 230° C., such as, for example, 2-ethoxyethylether, also known as diethylene glycol diethyl ether. Various other ethers of diethylene glycol may also be suitable, such as the dimethyl, dipropyl, dibutyl and dihexyl ethers. Mixed ethers such as the methylethyl ether of diethylene glycol are also suitable, as are aromatic ethers such as diphenyloxide. Hydrocarbon solvents may be useful, including high boiling materials such as 1,2-diphenylethane. The inert solvent should have solubility properties that allow the reaction to proceed at a reasonable rate, particularly by accommodating the solubility of the polar intermediate (or its salt complex).

When the partial esterification reaction is carried out in the presence of an inert solvent, alcohols with boiling points below 160° C. may be used. In particular, such alcohols with boiling points as low as about 100° C. may be used in conjunction with a high boiling solvent. Particularly, non-halogenated, non-sulfur-containing, non-nitrogen-containing alcohols with boiling points above about 130° C. may be used. Branched chain alcohols are particularly effective.

Examples of appropriate alcohols with boiling points lower than about 160° C. include 2-ethoxyethanol, amyl alcohol, 2-methyl-1-butanol, 3-methyl-1-butanol, 3-ethoxy-1-propanol, 2-ethyl-1-butanol, 4-methyl-2-pentanol, 2,4-dimethyl-3-pentanol, acetol, 2-butyne-1-ol, 3-butyn-1-ol, 1-pentyn-3-ol, 2-pentyn-1-ol, 3-pentyn-1-ol, 4-pentyn-1-ol, 4-pentyn-2-ol, cyclobutanemethanol, 3-methyl-2-buten-1-ol, 3-methyl-3-buten-1-ol, 2-penten-1-ol, 4-penten-1-ol, 1-pentanol, cyclohexanol, 1-hexen-3-ol, 2-hexen-1-ol, 3-hexen-1-ol, 4-hexen-1-ol, 5-hexen-1-ol, 1-methylcyclopentanol, 2-methylcyclopentanol, 3-methylcyclopentanol, 4-methyl-3-penten-1-ol, 3,3-dimethyl-1-butanol, 1-hexanol, 2-hexanol, 3-hexanol, 2-methyl-1-pentanol, 3-methyl-1-pentanol, 3-methyl-2-pentanol, t-butyldimethylsilanol, 1-ethynylcyclopentanol, 1,6-heptadien-4-ol, 2,2-dimethyl-3-pentanol, 2,3-dimethyl-3-pentanol, 4,4-dimethyl-2-pentanol, 3-ethyl-3-pentanol, 2-methyl-2-hexanol, 2-methyl-3-hexanol, 5-methyl-2-hexanol, 3,5-dimethyl-1-hexyn-3-ol, 2-chloroethanol, 2,2,3,3-tetrafluoro-1-propanol, propargyl alcohol, 2-chloro-2-propene-1-ol, 1-bromo-2-propanol, 1-chloro-2-propanol, 2-methoxyethanol, 2-(methylsulfonyl)ethanol, 3-butyn-1-ol, 3-buten-1-ol, crotyl alcohol, cyclobutanol, cyclopropanemethanol, 2-methyl-2-propen-1-ol, 1-chloro-2-methyl-2-propanol, 1-butanol, 2-butanol, 2-methyl-1-propanol, 1-methoxy-2-propanol, N,N-dimethylethanolamine, (trimethylsilyl)methanol, 2-methyl-3-butyn-2-ol, 1,4-pentadien-3-ol, 2-methyl-3-buten-1-ol, a-methylcyclopropanemethanol, 1-methylcyclopropanemethanol, 1-penten-3-ol, 3-penten-2-ol, 4-penten-2-ol, t-amyl alcohol, 3-methyl-2-butanol, neopentylalcohol, 2-pentanol, 3-pentanol, 1-(trimethylsilyl)ethanol, 3-methyl-1-pentyn-3-ol, 3-methyl-1-penten-3-ol, 2,3-dimethyl-2-butanol, 3,3-dimethyl-2-butanol, 2-methyl-2-pentanol, 2-methyl-3-pentanol, 3-methyl-3-pentanol, 1-methyl-2-piperidinemethanol, 1-methyl-3-piperidinemethanol, and 1-diethylamino-2-propanol.

Of these, acetol, 2-butyne-1-ol, 3-butyn-1-ol, 1-pentyn-3-ol, 2-pentyn-1-ol, 3-pentyn-1-ol, 4-pentyn-1-ol, 4-pentyn-2-ol, cyclobutanemethanol, 3-methyl-2-buten-1-ol, 3-methyl-3-buten-1-ol, 2-penten-1-ol, 4-penten-1-ol, 1-pentanol, cyclohexanol, 1-hexen-3-ol, 2-hexen-1-ol, 3-hexen-1-ol, 4-hexen-1-ol, 5-hexen-1-ol, 1-methylcyclopentanol, 2-methylcyclopentanol, 3-methylcyclopentanol, 4-methyl-3-penten-1-ol, 3,3-dimethyl-1-butanol, 1-hexanol, 2-hexanol, 3-hexanol, 2-methyl-1-pentanol, 3-methyl-1-pentanol, 3-methyl-2-pentanol, t-butyldimethylsilanol, 1-ethynylcyclopentanol, 1,6-heptadien-4-ol, 2,2-dimethyl-3-pentanol, 2,3-dimethyl-3-pentanol, 4,4-dimethyl-2-pentanol, 3-ethyl-3-pentanol, 2-methyl-2-hexanol, 2-methyl-3-hexanol, 5-methyl-2-hexanol and 3,5-dimethyl-1-hexyn-3-ol are preferred, while 2-ethoxyethanol, amyl alcohol, 2-methyl-1-butanol, 3-methyl-1-butanol, 3-ethoxy-1-propanol, 2-ethyl-1-butanol, 4-methyl-2-pentanol and 2,4-dimethyl-3-pentanol are particularly useful.

The second step of the process involves reacting the tetrabromophthalate half-ester intermediate mixture, either by a non-continuous process or in a continuous fashion, with a catalyst in one or more suitable reactors under conditions that favor decarboxylation over esterification to produce a benzoate-containing product mixture. A stirred tank reactor has been found to be a suitable reactor. However, it is also contemplated that tube reactors may also be used. Furthermore, feeding the tetrabromophthalate half-ester to multiple reactors connected in series has demonstrated unpredictably favorable results.

The catalyst used in the second step should be a catalyst that favors decarboxylation over esterification. Examples of such catalysts include alkali carbonates, alkali bicarbonates and caustic alkalis. Sodium and potassium carbonate and bicarbonate, lithium carbonate and sodium aluminate may be particularly useful. As is noted above, these compounds may also be used as a neutralizing agent in the partial esterification step to neutralize any residual mineral acid.

The catalyst loading may affect the product ratio of tetrabromobenzoate ester to tetrabromophthalate ester. For instance, in the case of a lower catalyst loading, the decarboxylation step may be slower, which may allow greater formation of diester. On the other hand, with a higher catalyst loading, lower amounts of diester are formed but increasing amounts of other by-products, such as the aromatic ether shown below, have been observed. In addition, the use of an excess of strong base as the catalyst/neutralization agent may also increase the formation of the aromatic either by-product shown below.

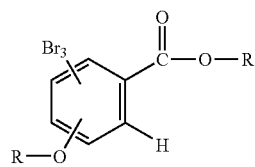

Aromatic Ether By-Product

Accordingly, low catalyst loading and use of a weak base as the catalyst/neutralization agent may be particularly useful. For instance, catalyst loading below 25 mole percent based upon the tetrabromophthalic anhydride charge has been particularly effective. More particularly, catalyst loading below 15 mole percent has demonstrated good results. Further favorable results have been achieved using catalyst loading between about 1 mole percent and 15 mole percent. It is believed that the selection of the proper catalyst, catalyst loading and reaction conditions, may result in a benzoate ester product having less than about 1% (GC area percent) of the aromatic ether by-product. It should also be understood that some catalysts yield a lighter colored product.

The conditions that favor decarboxylation may also include reaction vessel temperatures above about 160° C. At lower temperatures, for example below about 160° C., the esterification reaction may compete significantly with the decarboxylation reaction resulting in an end product containing a substantial amount of the tetrabromophthalic diester. More particularly, temperatures above about 180° C. have been found to favor the decarboxylation reaction over the esterification reaction, and temperatures below about 215° C. are particularly useful. Temperatures between about 190° C. and about 215° C. have been shown to favor considerably decarboxylation. Moreover, temperatures between about 190° C. and about 210° C. have produced favorable results. More particularly, temperatures between 200° C. and 205° C. have produced particularly favorable results.

While not wishing to be bound by theory, it is believed that heating the half-ester intermediate mixture from the lower temperatures in the first step to the decarboxylation favorable temperatures may permit the increased formation of the diester and may prolong the reaction time. Consequently, it is recommended that the half-ester intermediate be fed to one or more decarboxylation reaction vessels already having a temperature within the decarboxylation favorable range. The resulting tetrabromobenzoate ester-containing product has a clear, light amber color and comprises at least about 85% tetrabromobenzoate ester, and more favorably at least about 90% tetrabromobenzoate ester.

In a related embodiment, the first step involves forming the half-ester intermediate mixture as described above. In the second step, the tetrabromophthalate half-ester intermediate mixture is fed, either by a batch process or in a continuous fashion, to one or more suitable reactors containing an amount of tetrabromobenzoate and having a temperature that favors decarboxylation over esterification. The half-ester intermediate reacts with a catalyst favoring decarboxylation over esterification as described above. The decarboxylation catalyst may be included in the half-ester feed stream or, alternatively, may be present in the reaction vessel with the tetrabromobenzoate ester. It may be useful to add the half-ester intermediate mixture to the reactor or reactors at a rate that prevents the reactor temperature from dropping below the favorable range.

As noted above, the second step of the process may be performed in non-continuous or continuous fashion. For instance, in the non-continuous operation of a tank reactor, the temperature and agitation are maintained until the reaction is complete, generally about 2-8 hours, with the composition of the product determined by liquid chromatography if so desired. After the reaction is complete, the tank reactor may be partially drained, leaving in the reactor an amount of crude product (a "heel") sufficient to permit agitation. The drained product washed and stripped of excess alcohol. The heel in the reactor at the temperature favoring decarboxylation may then accept more half-ester intermediate mixture and aid in rapidly increasing the temperature of the half-ester intermediate mixture into the temperature range favoring decarboxylation. The high temperature decarboxylation process may be thus repeated. The resulting tetrabromobenzoate ester-containing product has a clear, light amber color and comprises at least about 75% tetrabromobenzoate ester, and more favorably at least about 85% tetrabromobenzoate ester. The amount of the heel remaining in the reactor influences the temperature of the blended heel and half-ester intermediate. In addition, the heat transfer characteristics of the tank reactor and the rate at which the half-ester intermediate mixture is added to the reactor also influences both the temperature of the blended heel and half-ester intermediate and the through put of the process.

In the continuous procedure, as the half-ester intermediate mixture is added, the product of the reactor may be removed to maintain a constant fill level. The product being removed during the continuous procedure may contain a quantity of half-ester. Therefore, it may be useful to feed the product continuously to one or more additional reactors connected in series and maintained at temperatures within the decarboxylation favorable range described above. It may also be advantageous to filter, wash, and/or vacuum strip the product to remove any excess unreacted alcohol. The unreacted alcohol may be recycled back into the process. The resulting tetrabromobenzoate ester-containing product has a clear, light amber color and comprises at least about 75% tetrabromobenzoate ester, and more favorably at least about 85% tetrabromobenzoate ester.

In an alternative embodiment, the half-ester intermediate is formed in-situ by feeding the starting materials, tetrabromophthalic anhydride and alcohol, either separately or as a slurry, directly to a heated reactor containing an amount of tetrabromobenzoate ester and having a temperature that favors decarboxylation over esterification. The acid neutralizing agent/decarboxylation catalyst may be included in the starting material feed stream or may be present in the reaction vessel with the tetrabromobenzoate ester. Because the full esterification of tetrabromophthalic anhydride is a two step process, and also because the decarboxylation step will not occur until the half-ester is formed, the half-ester forms first followed by the competing diesterification and decarboxylation reactions. The elevated temperature of the heated reactor and the presence of a decarboxylation catalyst promotes the formation of the tetrabromobenzoate ester over the diester.

The process of this embodiment may also be conducted in non-continuous form or continuous form. For example, in one non-continuous form of the embodiment, a tetrabromobenzoate ester and decarboxylation catalyst may be added to a reactor, such as a stirred tank reactor, filling the reactor to between about 10% and about 50% full by volume, more preferably to between about 20% and about 50% full, and even more advantageously to between about 20% and about 30% full. The reactor may then be heated to the previously described temperatures that favor decarboxylation over esterification. The starting materials, namely tetrabromophthalic anhydride and alcohol, may then be added to the hot tetrabromobenzoate ester mixture with agitation and at a rate that prevents the temperature from falling below the decarboxylation favorable range and until the reactor reaches a desired fill level. The decarboxylation catalyst may either be charged to the reactor along with the tetrabromobenzoate ester, or may be added along with the starting materials. As described previously, the amount of decarboxylation catalyst will be between about 1 mole % and about 25 mole % based on the tetrabromophthalic anhydride. The temperature and agitation are maintained until the reaction is complete, generally about 2-8 hours, with the composition of the product determined by liquid chromatography if so desired. After the reaction is complete, the reactor may be partially drained, and the drained product washed and stripped of excess alcohol. The crude product remaining in the reactor may then accept more starting materials and the high temperature decarboxylation process may be repeated.

In a related embodiment, the addition of the starting materials to the hot reactor of tetrabromobenzoate ester may be conducted in a continuous fashion. More specifically, a reaction vessel may be filled to between about 60% and about 90% by volume with tetrabromobenzoate ester and decarboxylation catalyst. Again, the mixture may be heated as previously described to temperatures that favor decarboxylation over esterification. The starting materials may then be added at a rate that prevents the temperature from falling below the favorable range. As the starting materials are added, the product of the vessel may be removed to maintain a constant fill level of between about 60% and about 90%. The product being removed may contain a quantity of half-ester. Therefore, the product may be fed continuously to one or more additional reactors, which are connected in series and are maintained at temperatures within the decarboxylation favorable range described above. The final product may optionally undergo one or more work-up or finishing steps, such as filtration, aqueous washings, and a vacuum strip to remove excess unreacted alcohol. The unreacted alcohol may be recycled back into the process. The resulting tetrabromobenzoate ester-containing product has a clear, light amber color and comprises at least about 75% tetrabromobenzoate ester, and more favorably at least about 85% tetrabromobenzoate ester.

Although the embodiments heretofore described use tetrabromophthalic anhydride as a starting material, it is contemplated that the process of the present invention may alternatively use tetrabromophthalic diacid as a starting material. However, the anhydride may be a more desirable starting material due to its commercial availability, its reactivity towards formation of the half-ester, and the minimal evolution of water during formation of the half-ester.

The ring-brominated benzoates produced in accordance with the invention are useful as flame retardants in a variety of polymer resin systems. For example, the bromobenzoate compound can be incorporated into thermoset polymers such as polyurethanes by including the bromobenzoate in the polyurethane mixture as the polymer is prepared. This process has been referred to as the "one-shot" technique, and is described with more particularity in common reference materials such as the Modern Plastics Encyclopedia, Vol. 71, No. 12 (1994).

The incorporation of bromobenzoates into polyvinyl chlorides may be accomplished either by including the desired tetrabromobenzoate ester in the mixture as the polyvinyl chloride is being formed, or by incorporating the bromobenzoate into polymerized polyvinyl chloride. Specific techniques for incorporating additives such as bromobenzoates into thermoplastics such as PVC are known to the art and may be used to accomplish that step.

It should be understood that the level of bromobenzoate incorporated into the polymer resin to provide an effective flame retarding amount will vary widely in accordance with many factors such as the particular resin used, the application contemplated, other additives present, etc. Typically, the bromobenzoate will be incorporated at levels above about 2% of the total system weight. Levels below about 50% are particularly effective, and levels between about 2% and 30% have demonstrated good results. Finally, levels between about 5% and 30% are exceptionally effective.

It should also be understood that other conventional additives may also be incorporated into the polymer systems. For example, the bromobenzoate product can be incorporated along with other brominated flame retardant compounds. Flame retardant materials such as oxides of Group V elements, especially antimony oxides, and/or phosphorous-containing compounds, can also be included. Additional conventional additives may include antioxidants, anti-static agents, colorants, fibrous reinforcements, fillers, foaming/blowing agents, catalysts, heat stabilizers, impact modifiers, lubricants, plasticizers, processing aids, UV light stabilizers, and crosslinking/curing agents.

Reference will now be made to specific examples using the process described above. It is to be understood that the examples are provided to more completely describe specific embodiments and the best mode of the invention, and that no limitation to the scope of the invention is intended thereby. All percentages given in the Examples and throughout this document are in weight percent unless specified otherwise.

EXAMPLE I

SYNTHESIS OF 2-ETHYLHEXYLTETRABROMOBENZOATE ESTER FROM TETRABROMOPHTHALIC ANHYDRIDE ACCORDING TO A PRIOR ART BATCH PROCESS

In this example, 2-ethylhexyltetrabromobenzoate ester was produced using the known batch process taught in U.S. Pat. No. 5,637,757 as described below. The reactants and their quantities used in the batch process are listed below in Table 1. The results are illustrated in Table 2.

TABLE 1

REACTANTS USED IN BOTH BATCH SYNTHESIS AND CONTINUOUS SYNTHESIS OF 2-ETHYLHEXYLTETRABROMOBENZOATE ESTER

| Reactant | Quantity (mole ratio) |
| --- | --- |
| Tetrabromophthalic anhydride | 1.00 |
| 2-Ethylhexanol | 2.50 |
| Sodium carbonate | 0.03 |

The reactants listed in Table 1 were charged into a glass lined reactor under agitation. The mixture was heated to 120° C. over a 1 hour period and then held at 120° C. for 2 hours. The resulting intermediate was essentially the 2-ethylhexyl half-ester of tetrabromophthalic anhydride dissolved in excess 2-ethylhexanol. Then, a portion of this mixture was then transferred to another glass lined reactor. The mixture was heated to 200° C. over a 1 hour period and then held at 200° C. for 8 hours. The water of the reaction (generated by the formation of the undesired tetrabromophthalate diester) was separated from the reaction product. At the end of 8 hours the reaction product was cooled and washed with water to remove the catalyst. The excess 2-ethylhexanol was striped off under vacuum at pressures of between about 3 mmHg and 7 mmHg to yield a clear amber liquid product, which was tested using High Performance Liquid Chromatography (HPLC) and the Gardner Color Test (ASTM D1544-98 Standard Test Method for Color of Transparent Liquids). The results of these tests are shown in Table 2 below.

EXAMPLE II

SYNTHESIS OF 2-ETHYLHEXYLTETRABROMOBENZOATE ESTER FROM TETRABROMOPHTHALIC ANHYDRIDE ACCORDING TO A CONTINUOUS PROCESS OF THE PRESENT INVENTION

In this example, 2-ethylhexyltetrabromobenzoate ester was produced using a method of the present invention and the reactants listed in Table 1. The results are listed below in Table 2.

The reactants listed in Table 1 were charged to a glass lined reactor under agitation. The mixture was heated from ambient temperature to 120° C. over a 1 hour period and then held at 120° C. for 2 hours. The reaction mixture was then continuously fed to the first of two glass lined reactors connected in series, both having a temperature of about 200° C. As the first reactor became full, the reaction mixture was drained to the second reactor. The reactors were maintained at 200° C. The residence time in each reactor was 3.4 hours. As the second reactor became full, the reaction material from the second reactor was drained to a glass-lined reaction vessel and washed with water. The reaction stream was then fed to a decanter to remove the water. The reaction stream was then fed to a wiped film evaporator (WFE) having an oil temperature of about 235° C. and vacuum pressure of between about 3 mmHg and 7 mmHg to remove the excess 2-ethylhexanol. The resulting product was a clear amber liquid that tested using HPLC and the Gardner Color Test and the results are listed below in Table 2.

TABLE 2

PRODUCT COMPOSITION AND COLOR RESULTS FOR BOTH BATCH SYNTHESIS AND CONTINUOUS SYNTHESIS OF 2-ETHYLHEXYLTETRABROMOBENZOATE ESTER

| | Batch Synthesis of 2-ethylhexyltetrabromobenzoate ester | Continuous Synthesis of 2-ethylhexyltetrabromobenzoate ester |
| --- | --- | --- |
| 2-Ethylhexyltetrabromobenzoate ester (weight %) | 73.31 | 90.22 |

TABLE 2-continued

PRODUCT COMPOSITION AND COLOR RESULTS FOR
BOTH BATCH SYNTHESIS AND CONTINUOUS SYNTHESIS
OF 2-ETHYLHEXYLTETRABROMOBENZOATE ESTER

|  | Batch Synthesis of 2-ethylhexyltetrabromobenzoate ester | Continuous Synthesis of 2-ethylhexyltetrabromobenzoate ester |
|---|---|---|
| Bis (2-Ethylhexyl) tetrabromophthalate (weight %) | 26.29 | 8.43 |
| Gardner Color | 11 | 6 |

The comparison of the results of both Example I and Example II, illustrated in Table 2, demonstrates that the process of the present invention, as compared to the prior art Batch Synthesis process, yields approximately 16.9% more of the targeted product, 2-ethylhexyltetrabromobenzoate ester. In addition, the reaction product of the present invention process has a lighter amber color, which is typically more desirable than the darker amber color of the product produced by the prior art Batch Synthesis process.

EXAMPLE III

NON-CONTINUOUS SYNTHESIS, ACCORDING TO THE PRESENT INVENTION, OF 2-ETHYLHEXYLTETRABROMOBENZOATE ESTER FROM TETRABROMOPHTHALIC ANHYDRIDE

In this example of the invention, an alternative non-continuous process according to one embodiment of the present invention was used to prepare 2-ethylhexyltetrabromobenzoate. The reactants are listed in Table 3.

TABLE 3

REACTANTS USED IN A NON-CONTINUOUS SYNTHESIS
OF 2-ETHYLHEXYLTETRABROMOBENZOATE ESTER

| Reactant | Amount, (wt %) | Mole Ratio |
|---|---|---|
| Tetrabromophthalic Anhydride | 52.38 | 1.00 |
| 2-Ethylhexanol | 36.95 | 2.50 |
| Sodium Bicarbonate | 0.86 | 0.09 |
| Crude Benzoate Ester* | 9.81 | — |

*Mixture of about 68% 2-ethylhexyltetrabromobenzoate ester and about 27% bis(2-ethylhexyltetrabromophthalate) from a previous run In a reactor equipped with an overhead stirrer and heating mantle, the tetrabromophthalic anhydride and 2-ethylhexanol were combined and slurried to form a first reaction mixture. This first reaction mixture was heated briefly to about 125° C. to form a nearly clear solution. The first reaction mixture was transferred to a heated, metered addition funnel, which was connected to a reactor. The crude benzoate ester from a previous run along with the sodium bicarbonate were charged into the second reactor and heated to 205° C. Over about a three hour period the first reaction mixture was metered into the second reactor, followed by a hold period of about six hours. The crude product was water washed and excess alcohol was stripped on a wiped film evaporator at a temperature of about 175° C. and a vacuum of between 3-5 mmHg. The finished product contained about 77% 2-ethylhexyltetra-bromobenzoate and 21% bis(2-ethylhexyl)tetrabromophthalate, and had a Gardner Color result of 9-10.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method for preparing tetrabromobenzoate ester from tetrabromophthalic anhydride comprising the steps of:
   combining the tetrabromophthalic anhydride and an alcohol in at least one reaction vessel to form a first reaction mixture;
   heating the first reaction mixture to a temperature that favors partial esterification over complete esterification to form a tetrabromophthalate half-ester intermediate mixture;
   feeding the tetrabromophthalate half-ester intermediate mixture and a catalyst comprising alkali carbonates, alkali bicarbonates and caustic alkalis to at least one heated reactor having a temperature that favors decarboxylation over esterification; and
   maintaining the at least one reactor at the temperature that favors decarboxylation over esterification to produce a tetrabromobenzoate ester-containing product.

2. The method of claim 1 wherein the temperature that favors partial esterification over complete esterification is greater than about 70° C.

3. The method of claim 2 wherein the temperature that favors partial esterification over complete esterification is between about 90° C. and about 130° C.

4. The method of claim 1 wherein the temperature that favors decarboxylation over esterification is above about 190° C.

5. The method of claim 4 wherein the temperature that favors decarboxylation over esterification is between about 190° C. and about 205° C.

6. The method of claim 1 wherein the alcohol has a boiling point between about 100° C. and about 230° C.

7. The method of claim 1 wherein the alcohol has the formula ROH, and wherein R is an organic group having up to about 30 carbon atoms.

8. The method of claim 1 wherein said step of combining the tetrabromophthalic anhydride and an alcohol occurs in the presence of an inert solvent.

9. The method of claim 8 wherein the inert solvent is an ether having a boiling point between about 160° C. and 230° C.

10. The method of claim 1 wherein the catalyst is a compound selected from the group consisting of carbonates, alkali bicarbonates, alkalis, and mixtures thereof.

11. The method of claim 1 wherein at least 85% of the tetrabromobenzoate ester-containing product consists of tetrabromobenzoate ester.

12. The method of claim 1 wherein the at least one reactor contains tetrabromobenzoate ester when feeding the tetrabromophthalate half-ester intermediate mixture to at least one heated reactor.

13. The method of claim 1 wherein the at least one reactor includes a plurality of heated reactors connected to one another in series.

14. The method of claim 13 wherein the first of the plurality of heated reactors contains tetrabromobenzoate ester when the tetrabromophthalate half-ester intermediate mixture is fed to at least one heated reactor.

15. The method of claim 1 wherein said step of feeding the tetrabromophthalate half-ester intermediate mixture is continuous such that the half-ester intermediate mixture is continuously fed to the at least one reactor, while the tetrabromobenzoate ester-containing product is continuously removed from the at least one reactor.

16. A method for preparing a flame retarded polymer resin comprising the steps of:

combining the tetrabromophthalic anhydride and an alcohol in at least one reaction vessel to form a first reaction mixture;

heating the first reaction mixture to a temperature that favors partial esterification over complete esterification to form a tetrabromophthalate half-ester intermediate mixture;

feeding the tetrabromophthalate half-ester intermediate mixture and a catalyst comprising alkali carbonates, alkali bicarbonates and caustic alkalis to at least one heated reactor having a temperature that favors decarboxylation over esterification;

maintaining the at least one reactor at the temperature that favors decarboxylation over esterification to produce tetrabromobenzoate ester;

preparing a polymer mixture; and adding the tetrabromobenzoate ester to the polymer mixture.

17. The method of claim 16 wherein the polymer mixture comprises polyvinyl chloride, polyurethane, or mixture thereof.

* * * * *